United States Patent
Rolfo et al.

(10) Patent No.: US 10,413,573 B2
(45) Date of Patent: Sep. 17, 2019

(54) CONDITIONED MEDIUM OBTAINED FROM PLACENTAL MESENCHYMAL STEM CELLS AND USE THEREOF IN THE THERAPEUTIC TREATMENT OF PREECLAMPSIA

(71) Applicant: CORION BIOTECH S.r.l., Turin (IT)

(72) Inventors: Alessandro Rolfo, Turin (IT); Tullia Todros, Turin (IT)

(73) Assignee: Corion Biotech S.R.L., Turin (IT)

( * ) Notice: Subject to any disclaimer, the term of this patent is extended or adjusted under 35 U.S.C. 154(b) by 0 days.

(21) Appl. No.: 15/489,817

(22) Filed: Apr. 18, 2017

(65) Prior Publication Data

US 2017/0216366 A1 Aug. 3, 2017

Related U.S. Application Data

(63) Continuation of application No. 14/367,604, filed as application No. PCT/IB2012/057611 on Dec. 21, 2012.

(30) Foreign Application Priority Data

Dec. 21, 2011 (IT) ............................. TO2011A1183

(51) Int. Cl.
| | |
|---|---|
| *A61K 35/50* | (2015.01) |
| *A61K 38/19* | (2006.01) |
| *A61K 38/20* | (2006.01) |
| *A61K 35/28* | (2015.01) |
| *C12N 5/073* | (2010.01) |

(52) U.S. Cl.
CPC .............. *A61K 35/50* (2013.01); *A61K 35/28* (2013.01); *A61K 38/19* (2013.01); *A61K 38/195* (2013.01); *A61K 38/204* (2013.01); *A61K 38/2053* (2013.01); *A61K 38/2066* (2013.01); *C12N 5/0605* (2013.01); *C12N 2502/025* (2013.01)

(58) Field of Classification Search
None
See application file for complete search history.

(56) References Cited

U.S. PATENT DOCUMENTS

| 2008/0226595 A1 | 9/2008 | Edinger et al. |
| 2012/0276215 A1 | 11/2012 | Riordan et al. |

OTHER PUBLICATIONS

Timmers et al., Stem Cell Research, 2008; 1: 129-137. (Year: 2008).*
Young, B.C. et al., "Pathogenesis of Preeclampsia," Annual Review of Pathology: Mechanisms of Disease, vol. 5, No. 1, Jan. 1, 2010, pp. 173-192.
Hwang, J.H. et al., "Cytokine Expression in Placenta-Derived Mesenchymal Stem Cells in Patients with Pre-eclampsia and Normal Pregnancies," Cytokine, Academic Press Ltd., Philadelphia, PA., vol. 49, No. 1, Jan. 1, 2010, pp. 95-101.
Huang, Y.C. et al., "Isolation of Mesenchymal Stem Cells from Human Placental Decidua Basalis and Resistance to Hypoxia and Serum Deprivation," Stem Cell Reviews and Reports, Humana Press Inc., US, vol. 5, No. 3, Sep. 1, 2009, pp. 247-255.
Portmann-Lanz, C.B. et al., "Neurogenic Characteristics of Placental Stem Cells in Preeclampsia," American Journal of Obstetrics & Gynecology, Mosby, St. Louis, MO, US, vol. 203, No. 4, Oct. 1, 2010, pp. 399.E1-399.E7.
Horn, A.P. et al., "Mesenchymal Stem Cell-Conditioned Medium Triggers Neuroinflammation and Reactive Species Generation in Organotypic Cultures of Rat Hippocampus," Stem Cells and Development Jul. 2011 LNKD-PUBMED:2095507, vol. 20, No. 7, Jul. 2011, pp. 1171-1181.
"Preparing and Storing Conditioned Medium," In: Anonymous: "Essentials of Stem Cell Biology. 2nd Edition.,", 2006, Elsevier, San Diego, CA, XP002671397. 1 page.
PCT International Search Report dated Nov. 3, 2013, International Application No. PCT/IB2012/057611, International Filing Date: Dec. 21, 2012, Applicant: Corton Biotech S.r.l., 4 pages.
Meads, C.A. et al., "Methods of Prediction and Prevention of Pre-Eclampsia: Systematic Reviews of Accuracy and Effectiveness Literature with Economic Modeling," Health Technology Assessment, 2008, vol. 12, No. 6 (Executive Summary), 6 pages.
Ruster, B. et al., "Mesenchymal Stem Cells Display Coordinated Rolling and Adhesion Behavior on Endothelial Cells," Blood, Dec. 1, 2006, vol. 108, No. 12, pp. 3938-3944.
Battula, V. L. et al. "Human placenta and bone marrow derived MSC cultured in serum-free, b-FGF-containing medium express cell surface frizzled-9 and SSEA-4 and give rise to multilineage differentiation" Differentiation, Apr. 2007, pp. 279-291, vol. 75. Iss. 4.
Hass, R. et al. "Different populations and sources of human mesenchymal stem cells (MSC): A comparison of adult and neonatal tissue-derived MSC" Cell Communication and Signaling, May 2011, 9:12, 14 pages.
MeSH entry for CCL2; downloaded Apr. 14, 2015 from ncbi.nlm.nih.gov/mesh/68018932; 3 pages total.
Borzychowski, A. M. et al. "Inflammation and pre-eclampsia.", Seminars in Fetal & Neonatal Medicine Oct. 2006, pp. 309-316, vol. 11, Iss. 5.
Liu, L. et al. "Mesenchymal Stem Cells Ameliorate Th1-Induced Pre-Eclampsia-Like Symptoms in Mice via the Suppression of TNF-α Expression" PLoS ONE, Feb. 2014, pp. 1-10, vol. 9, Iss. 2.
The abstract by Rolfo et al., Placenta 32 Abstract, Sep. 2011; #P1.110; p. A64.

* cited by examiner

*Primary Examiner* — Christina M Borgeest
(74) *Attorney, Agent, or Firm* — Rothwell, Figg, Ernst & Manbeck, P.C.

(57) ABSTRACT

The present invention relates to a conditioned medium (CM) which is obtained by culturing, in a liquid culture medium, placental mesenchymal stem cells isolated from the placental tissue of pregnant women who not affected by preeclampsia. The conditioned medium of the present invention includes at least IL-6, IL-8 and MCP-1 proteins. The conditioned medium of the present invention is effective for the therapeutic treatment of preeclampsia.

4 Claims, 1 Drawing Sheet

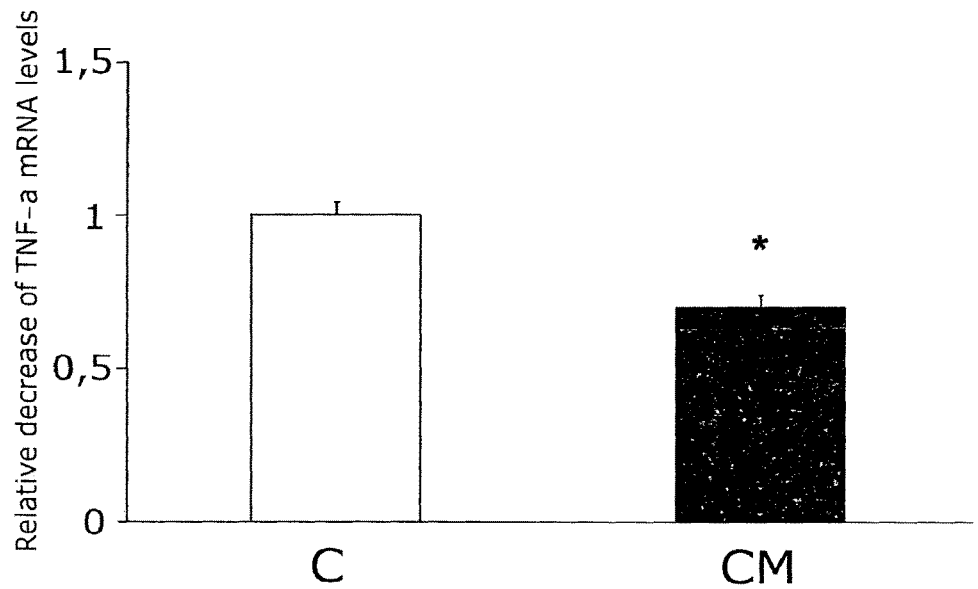
C = Preeclamptic placental explants treated by non-conditioned culture medium
CM = Preeclamptic placental explants treated by culture medium conditioned by physiological PDMSCs
* = $p<0.05$ ized by maternal hypertension in previously normotensive women, proteinuria higher than 0.3 grams per day and generalized edema. Together with a compromised maternal health condition, the preeclamptic syndrome presents several risk factors for the fetus, being generally accompanied by intra-uterine fetal growth defects (intra-uterine fetal growth restriction).

CONDITIONED MEDIUM OBTAINED FROM PLACENTAL MESENCHYMAL STEM CELLS AND USE THEREOF IN THE THERAPEUTIC TREATMENT OF PREECLAMPSIA

CROSS-REFERENCE TO RELATED APPLICATIONS

The present application is a continuation of U.S. patent application Ser. No. 14/367,604 filed on 20 Jun. 2014, which is a national stage filing under 35 U.S.C. § 371 of PCT/IB2012/057611, filed on 21 Dec. 2012, which in turn claims priority to Italian Patent Application No. TO2011A001183 filed on 21 Dec. 2011. Each of these applications is incorporated herein in its entirety.

Preeclampsia (PE) is a severe pregnancy-related syndrome that affects 5-10% of all pregnant women, thus representing one of the main causes of fetal-maternal mortality and morbidity worldwide. Preeclampsia is a multisystemic disorder that manifests itself during the third trimester of pregnancy with a symptomotology characterized by maternal hypertension in previously normotensive women, proteinuria higher than 0.3 grams per day and generalized edema. Together with a compromised maternal health condition, the preeclamptic syndrome presents several risk factors for the fetus, being generally accompanied by intra-uterine fetal growth defects (intra-uterine fetal growth restriction).

Despite preeclampsia has been subject of intense investigation by the clinical-scientific community during the past decade, its etiopathogenesis still remains unclear and the only effective therapeutic treatment is a timed, and often premature, delivery. Even when the newborn survives to pre-term delivery, this intervention presents several risks like pulmonary diseases, retinopathy, cerebral palsy, mental retardation, cardiovascular and metabolic diseases that could also manifest during adult age. Furthermore, even though preeclampsia resolves at delivery with placenta removal, it could determine severe maternal long term complications. Among these, it was reported a significant higher risk of chronic hypertension, diabetes mellitus, chronic kidney disease and cardiovascular diseases.

On these basis, it is evident that this severe pregnancy-related syndrome has important clinical and social-economical implications. Therefore, it is necessary to develop effective pharmacological treatments able to act on the broad range of etiopathogenic factors typical of preeclampsia, thus allowing to extend the time of delivery and to avoid severe and potentially permanent injuries to both the mother and the newborn.

Despite PE suddenly manifests during the third trimester of pregnancy, it is likely that it originates during the first trimester, time when it starts the delicate process of trophoblast differentiation and invasion. Histomorphological studies have highlighted that preeclamptic pregnancies are characterized by an aberrant placentation process with defective maternal spiral arteries remodeling due to shallow invasion of the decidua by the trophoblast. These defects lead to a prolonged reduction of utero-placental perfusion, with consequent ischemic damage and release of toxic molecules responsible for the exacerbated placental and maternal inflammation and generalized endothelial damage. TNF-alpha ("Tumor necrosis factor alpha") plays a pivotal role in the activation and propagation of the inflammatory response. TNF-alpha serum and placenta expression has been found significantly increased in pregnant women affected by preeclampsia compared to women with a physiological pregnancy. Moreover, it is known that TNF-alpha is co-responsible for the reduced trophoblast invasivity typical of this pregnancy-related syndrome.

Placenta is a complex organ made of different tissues like the mesenchyme, that represents the most abundant placental cellular component. Recent studies have demonstrated that placental mesenchyme and amniotic membranes contain a unique cellular population with a mesenchymal-stem phenotype (Huang Y C, Yang Z M, Chen X H, Tan M Y, Wang J, Li X Q, et al. *Isolation of mesenchymal stem cells from human placental decidua basalis and resistance to hypoxia and serum deprivation*. Stem Cell Rev. 2009; 5 (3):247-55). These cells, named placental mesenchymal stem cells (PDMSC), are characterized by very elevated proliferative, differentiative and self-renewal potentials as well as by immunosuppressive and anti-inflammatory activities. Moreover, PDMSCs play a key role in the regulation of reparative and proliferative processes of neighboring cells. Mister B and colleagues reported that MSCs possess the ability to spontaneously migrate towards injured tissues and organs in order to take part in the reparative process (Mister B, Göttig S, Ludwig R J, Bistrian R, Müller S, Seifried E, et al. *Mesenchymal stem cells display coordinated rolling and adhesion behavior on endothelial cells*. Blood. 2006; 108 (12):3938-44).

On the basis of the unique functional plasticity and differentiation properties described above as well of the high accessibility and use of placenta per se, placental mesenchymal stem cells became subject of investigation mainly in the field of regenerative medicine. Moreover, to further support PDMSCs clinical use in this field, mesenchymal stem cells are non-immunogenic, since they do not express HLA Type II and co-stimulatory molecules (CD80, CD86, CD40) necessary to directly stimulate T lymphocytes, and they are resistant to cytotoxic T lymphocytes-mediated lysis. The distinctive immunological features of these cells suggest that they could play an important role in the maintenance of fetal-maternal tolerance.

As it will be described in more detail in the following experimental section, the present inventors observed that the conditioned medium (CM) obtained by culturing placental mesenchymal stem cells in a liquid culture medium exerts a remarkable anti-inflammatory effect on placental villous explants obtained from pregnancies complicated by preeclampsia. In particular, the inventors reported that the treatment of pathologic villous explants by using culture medium conditioned by PDMSC obtained from the placenta of women not affected by preeclampsia, induces a significant and extraordinary gene expression reduction of TNF-alpha pro-inflammatory cytokine.

Therefore, this allows to efficiently use the conditioned medium obtained from placental mesenchymal stem cells cultured in a liquid medium for the therapeutic treatment of preeclampsia.

In order to identify the proteins secreted by PDMSCs cells that most probably all together contribute to the beneficial effects of CM which were previously described, the inventors subjected the CM mentioned above to proteomic analysis by using a commercial array containing antibodies capable of specifically and simultaneously recognizing several cytokines, chemokines and growth factors. The data obtained from this proteomic analysis revealed the presence of several factors among which are prominent interleukin 6 (IL-6), interleukin 10 (IL-10) and monocyte chemotactic protein-1 (MCP-1).

Therefore, the invention relates to a conditioned medium obtainable by culturing a placental mesenchymal stem cell derived from the placenta of a pregnant woman not affected by preeclampsia, in a liquid culture medium, the conditioned medium containing at least IL-6, IL-10 and MCP-1 factors. This conditioned medium is particularly useful for the therapeutic treatment of preeclampsia. The invention also relates to a method of producing the conditioned medium of the invention, the use of the conditioned medium of the invention for preparing a medicament for the therapeutic treatment of preeclampsia, and anti-inflammatory therapeutic treatment methods in patients affected by preeclampsia, everything as defined in the appended claims which form an integral part of the present description.

In the present description, the term "placental mesenchymal stem cell" indicates a mesenchymal stem cell isolated from the placenta of a pregnant woman not affected by preeclampsia. The therapeutic effectiveness of these cells is really surprising, since the conditioned medium obtained by culturing mesenchymal stem cells isolated from preeclamptic placentae does not exert any anti-inflammatory effect on pathological placental explants, contrary to what has been described for mesenchymal stem cells derived from physiological placentae.

Placental mesenchymal stem cells can belong to different cellular populations, depending on the placental tissue of origin. Actually, human placenta has a unique structure including both fetal tissue, such as chorion (chorion leave and chorion frondosum) and amnion, as well as maternal tissues, such as decidua.

In a preferred embodiment, the conditioned medium of the invention is obtained by culturing placental mesenchymal stem cells of chorionic origin. Preferably, chorionic mesenchymal stem cells presents the surface antigens shown in the following table, as detected by cytofluorimetric analysis.

| Marker | Cytofluorimetric analysis |
| --- | --- |
| HLA I | + |
| CD105 (Endoglin) | + |
| CD166 (ALCAM) | + |
| CD90 (Thy-1) | + |
| CD73 (5'-nucleotidase) | + |
| CD34 | − |
| HLA-DR | − |
| CD133 (Prominin-1) | − |
| CD20 | − |
| CD326 (EpCAM) | − |
| CD31 (PECAM-1) | − |
| CD45 (PTPRC) | − |
| CD14 | − |

Alternatively, to prepare the conditioned medium of the invention a mesenchymal stem cells derived from the amnion, presenting the surface antigens described in the above-reported table, will be used, The conditioned medium of the invention includes at least the factors IL-6, IL-10 and MCP-1, which are cell-secreted cytokines known per se, and which are capable of exerting a significant anti-inflammatory effect.

In particular, the anti-inflammatory mechanism of IL-6 involves both the inhibition of TNF-alpha production and, at the same time, the induction of secretion of Interleukin-10, a factor able to inhibit the synthesis of other inflammatory cytokines. On the contrary, the anti-inflammatory effect of MCP-1 is mediated by a potent inhibitory action towards lymphocyte cell populations.

In addition to the above mentioned cytokines, PDMSC conditioned medium analysis, performed by using RayBio® Human Cytokine Antibody Array 5 kit, revealed the presence of other functional modulators secreted by placental mesenchymal stem cells, thus identifying a distinct protein expression profile.

Therefore, in yet another embodiment, the conditioned medium of the invention comprises a further cell-secreted factor selected from the group consisting of: ENA-78, GCSF, GRO, GRO-alpha, IL-6, IL-7, IL-8, MCP-1, MCP-2, MCSF, MDC, ANGIOGENIN, ONCOSTATIN m, VEGF, BDNF, BLC, CKb 8-1, EOTAXIN 2, EOTAXIN 3, FLT-3 LIGAND, FRACTALKINE, GCP-2, GDNF, HGF, IGFBP-1, IGFBP-2, IGFBP-4, IP-10, LIF, LIGHT, MCP-4, MIF, MIP-3alpha, NAP-2, NT-3, OSTEOPONTIN, OSTOPROTEGERIN, TGF-beta 2, TIMP-1, TIMP-2, RANTES, IGFBP-3, IL1b, IL-3, MIP-1b, PIGF, IL-1a, I309, FGF9, TARC, PDGF-bb, LEPTIN, TNF-alpha and any combination thereof. In a preferred embodiment, the further cell-secreted factor which is present in the conditioned medium of the invention is interleukin 8 (IL-8), which is expressed and secreted by the cells in a high amount into the conditioned medium.

In a preferred embodiment, the conditioned medium is used for the therapeutic treatment of preeclampsia.

Therefore, an additional aspect of the invention is the conditioned medium of the present invention for use in the therapeutic treatment of preeclampsia.

Since PDMSC possess the unique feature of being non-immunogenic, the conditioned medium of the invention comprises, according to an embodiment, a cellular fraction which consists of the placental mesenchymal stem cells for which it was obtained. Alternatively, the conditioned medium is free of cellular components.

As an alternative to the conditioned medium, placental mesenchymal stem cells derived from pregnant women not affected by preeclampsia, preferably of chorionic origin or as an alternative of amniotic origin, may be used for the therapeutic treatment of preeclampsia.

As previously mentioned, the term "placental", in the context of the present invention, indicates the derivation from physiological pregnancies not affected by preeclampsia.

Therefore, a further aspect of the present invention is a placental mesenchymal stem cell derived from a pregnant woman not affected by preeclampsia, preferably of chorionic origin or as an alternative of amniotic origin, for use in the therapeutic treatment of preeclampsia.

The scope of the present invention also includes a method of preparing the conditioned medium described above, which comprises the steps of:

(i) culturing placental mesenchymal stem cells from the placenta of a pregnant woman not affected by preeclampsia in a serum-free liquid basal culture medium for at least 3 hours;

(ii) separating the cell fraction from the liquid culture medium, thereby obtaining a conditioned medium comprising a combination of factors secreted by said placental mesenchymal stem cells, said conditioned medium comprising at least interleukin-6 (IL-6), interleukin-10 (IL-10) and monocyte chemoattractant protein 1 (MCP-1).

Preferably, the conditioned medium obtainable by the method of the invention comprises a further cell-secreted factor which is selected from the group consisting of ENA-78, GCSF, GRO, GRO-alpha, IL-6, IL-7, IL-8, MCP-1, MCP-2, MCSF, MDC, ANGIOGENIN, ONCOSTATIN m, VEGF, BDNF, BLC, CKb 8-1, EOTAXIN 2, EOTAXIN 3, FLT-3 LIGAND, FRACTALKINE, GCP-2, GDNF, HGF, IGFBP-1, IGFBP-2, IGFBP-4, IP-10, LIF, LIGHT, MCP-4, MIF, MIP-3alpha, NAP-2, NT-3, OSTEOPONTIN, OSTOPROTEGERIN, TGF-beta 2, TIMP-1, TIMP-2, RANTES, IGFBP-3, IL1b, IL-3, MIP-1b, PIGF, IL-1a, I309, FGF9, TARC, PDGF-bb, LEPTIN, TNF-alpha and any combination thereof.

In a preferred embodiment, the further cell-secreted factor which is present in the conditioned medium of the invention is Interleukin-8 (IL-8), which is expressed and secreted in high amounts by the cells in the conditioned medium.

In a further embodiment, the method of the invention also comprises step (iv) of isolating from the conditioned medium obtained in step (iii) of one or more factors secreted from the placental mesenchymal stem cells.

In the context of the present description, the term "basal" indicates a culture medium containing inorganic salts, amino acids and vitamins usually required to support growth of mammalian cells not having particular nutritional requirements. By way of example and without limitation, the following liquid culture media, that differ for salts and amino acids content, are mentioned: Basal Medium Eagles (BME), Minimum Essential Medium (MEM), Dulbecco's Modified Eagle's Medium (DMEM), Nutrient Mixture F-10 (HAM's F-10) and Nutrient Mixture F-12 (HAM's F-12). The culture media mentioned above are cited as illustrative examples of culture medium suitable for use in the production of the conditioned medium of the invention.

The selection of the most appropriate culture medium is within the reach of those skilled in the art.

According to the method of the invention, the culture medium is not supplemented with serum, in order to avoid that the growth factors contained in the serum interfere and alter the effects produced by specific factors secreted by PDMSC.

Before collecting the conditioned medium, placental mesenchymal stem cells are cultured for a time sufficient to allow their adhesion to the culture substrate, their multiplication and the secretion of the components which characterize the above mentioned medium and make it beneficially effective for the therapeutic treatment of preeclampsia. Therefore, placental mesenchymal stem cells are cultured for at least 3 hours, preferably for at least 12, at least 24 hours, at least 48 hours, at least 72 hours or even more.

In order to separate the cellular fraction from the medium conditioned by PDMSC, different methods known per se may be used. For example, the conditioned medium of the invention can be processed by filtration using filters of adequate porosity which allow to retain in suspension the cellular elements and their residues. Alternatively, the separation of the conditioned medium from PDMSC can be achieved by centrifugation followed by cell sedimentation. Therefore, in a preferred embodiment, the step of separation of the conditioned medium from the cellular component is performed by filtration or centrifugation or a combination of both. The selection of the separation method is within the knowledge and skills of skilled in the art. Even the purification of one or more of the cell-secreted factors contained in the conditioned medium is performed by methods known per se whose selection and correct use are within the reach of those skilled in the art.

In order to exert an effective therapeutic activity, the conditioned medium object of the invention or the stem cell of the invention are administered to pregnant women affected by this syndrome. Therefore, a further object of the invention is the use of a conditioned medium as defined above or a placental mesenchymal stem cell derived from pregnant women not affected by preeclampsia, for the preparation of a medicament for the therapeutic treatment of preeclampsia.

Preferably, the medicament is in a pharmaceutical form suitable for systemic administration, more preferably by injection, in order to ensure its diffusion into the circulation. Clearly, the use of injective systems of any type, whose selection is within the knowledge of the person skilled in the art, falls within the scope of the present invention.

The following examples are provided for illustrative, non-limitative purposes of the scope of the invention as defined in the appended claims.

EXAMPLE 1

Placenta-Derived Mesenchymal Stem Cells Isolation (PDMSCs)

Placenta-derived Mesenchymal Stem Cells (PDMSCs) were isolated from placentae obtained from healthy and normotensive pregnant women with physiological pregnancy. Placental tissue collection and sampling were performed after delivery and after obtaining informed consent in accordance with the guidelines of the ethics committee of OIRM Sant'Anna—Ospedale Mauriziano of Turin. Pregnancies affected by congenital malformations, chromosomal anomalies (in structure or number), infectious diseases, diabetes, cardiovascular and metabolic syndromes were excluded.

Placental membranes (amnion and chorion leave) were mechanically separated from the placenta.

Full-thickness tissue biopsies were excised from the placental basal plate (portion of the placenta formed by chorionic villi and adherent to the uterine wall) after mechanical removal of the decidua basalis (tissue made of maternal endometrial cells modified by the interaction with the syncitiotrophoblast).

Then, placental tissue biopsies were washed several times at room temperature by using sterile HBSS (Hank's Buffered Salt Solution, in aqueous solution) (Gibco, Invitrogen by Life Technologies), in order to completely remove blood residues.

Biopsies were next mechanically homogenized and processed by enzymatic digestion using 100 U/ml Collagenase I, Gibco, Invitrogen by Life Technologies), 5 µg/ml Deoxyribonuclease I (DNAse I, Invitrogen by Life Technologies) in DMEM LG (Dulbecco's Modified Minimum Essential Medium Low Glucose without L-glutamina and without Fetal Bovine Serum-FBS), at 37° C. for 3 hours in a shacking thermostated water bath.

The resulting cell suspension was then centrifuged for 5 seconds, 540 g at 4° C. in order to remove the undigested tissue residues. The supernatant was collected and filtered through Cells strainer filters with pores of 70 microns in diameter. After filtration, the solution was centrifuged for 5 minutes at 540 g, 4° C. in order to pellet the cells. The supernatant was then discarded and cells were re-suspended in sterile HBSS (30 ml for every 30 grams of original tissue).

A volume of Ficoll Paque Premium 1,073 (GE Healthcare Europe) was layered under the solution obtained as described above, in the proportion of 1:3 relative to the starting volume. The preparation was centrifuged for 20 minutes at 540 g 20° C. and mononuclear cell ring, positioned in the middle phase of the gradient, was collected, resuspended in HBSS (50 ml for every 30 grams of original tissue) and centrifuged 10 minutes at 540 g, 20° C. in order to remove Ficoll residues.

After centrifugation, the supernatant was discarded and the cells re-suspended in DMEM LG supplemented with 10% FBS (Gibco, Invitrogen by Life Technologies) and 0.1% Gentamicin. The cells were then plated in cell culture flasks and incubated at 37° C. and 5% $CO_2$.

Cells were maintained in culture at 37° C., 5% $CO_2$. At 90% of confluence, cells were splitted by treatment with trypsin TrypLE Express (trypsin of vegetable origin without animal derivates, GMP certified, Invitrogen Life Technologies) in order to promote cell expansion.

In order to isolate mesenchymal stem cells from amnion, membranes were repeatedly washed at room temperature with sterile HBSS (Hank's Buffered Salt Solution, in aqueous solution) and the amnion was mechanically separated from the chorion. The amnion was then processed by enzymatic digestion, separated and cultured as described above for mesenchymal stem cells derived from placental basal plate (chorionic portion).

EXAMPLE 2

Characterization of PDMSCs

Mesenchymal stem cells isolated from term physiological placentae (basal plate-chorionic portion) as described in Example 1, were characterized by analyzing the main surface antigenic markers typical of this cell type by cytofluorimetric assay.

The presence or absence of these antigens was evaluated by using monoclonal antibodies conjugated with fluorocromes (Myltenyi, Bologna, Italy). By fluorescence evaluation, it was demonstrated that all PDMSC cell lines were positive for the expression of surface markers CD105, CD166, CD90 and CD73 and negative for the expression of HLAII, CD34, CD133, CD20, CD326, CD31, CD45 and CD14, thus showing an appropriate mesenchymal phenotype and excluding any contamination from epithelial/trophoblast cells and haematopoietic progenitors. Moreover, the cell phenotype analysis was also conducted by performing RT-PCR experiments, that showed that all PDMSCs also express the Oct4 (Octamer-binding transcription factor 4) and NANOG (Homeobox protein NANOG) genes, typical of embryonic stem cells.

In order to evaluate PDMSCs stemness, at the third passage of culture cells were examined for their differentiation potential in three different lineage: osteoblasts, adipocytes and chondroblasts. PDMSCs differentiation was obtained by using specific induction media. For osteogenic differentiation, cell cultures were incubated in α-MEM supplemented with 20% FCS, 100 U/ml penicillin, 100 µg/ml streptomycin, 2 mM L-glutamine, 20 mM β-phosphate-glycerol, 100 nM dexamethasone and 250 µM ascorbate-2-phosphate. For adipogenic differentiation, cell cultures were incubated with α-MEM supplemented with 20% FCS, 100 U/ml penicillin, 100 µg/ml streptomycin, 12 mM L-glutamine, 5 µg/ml insulin, 50 µM indomethacin, $1\times10^{-6}$ M dexamethasone and 0.5 µM 3-isobutyl-1-methylxanthine. For chondrogenic differentiation, the cultures were incubated in Chondrocyte Basal Medium supplemented with R3-IGF-1 1 mL, bFGF 2.5 ML, 0.5 mL transferrin, bovine insulin 1 M, 25 mL FBS and gentamicin/amphotericin-B 0.5 mL. The medium was changed twice a week for three weeks. Cellular differentiation was assessed by using appropriate colorations. Osteoblast differentiation was assessed by staining with Alizarin Red S. Alizarin determines the formation of insoluble and intensely colored calcium plaques, thus allowing to highlight the bone matrix. Chondrogenic differentiation was assessed by Alcian Blue staining that form salt bridges between acid mucopolysaccharides polyanions, letting glycosaminoglycans be colored of blue. Adipogenic differentiation was detected by Oil Red staining, which highlights the lipids solubilized by the solvent present in the dye solution and the red-colored fat deposits.

EXAMPLE 3

Conditioned Medium Production

In order to obtain the conditioned medium of the invention, PDMSCs were plated between passages 3 to 5, time when they reached the appropriate degree of purity, as demonstrated by the absence of trophoblastic and/or haematopoietic contaminants derived from the original placental tissue. More specifically, cells were plated at a density of $1\times10^5$ cells/ml in DMEM LG without Fetal Bovine Serum (FBS) at a temperature of 37° C. and 5% $CO_2$. PDMSCs were cultured for at least 3 hours to a week or more. Conditioned media were then collected at the established time points, centrifuged and/or filtered to remove contaminant cellular debris. When necessary, conditioned media obtained as just described can be preserved by freezing them at −80° C.

EXAMPLE 4

Conditioned Medium Analysis by Cytokine Array

Commercially available RayBio® Human Cytokine Antibody Array 5 was used, following manufacturer instructions, in order to investigate the cell-secreted cytokines present in the PDMSCs conditioned medium of the invention. This specific cytokine array kit allows to contemporary detect 80 different cytokines present in the same sample. Specifically, the procedure is based on antibodies spotted on a membrane and able to recognize and capture cytokines when present in the analyzed sample. In the context of this experiment, the signals generated on the array membrane at the sites of immune-complex formation were quantified by densitometric analysis using the ImageQuant software. Expression levels of the so identified cytokines were not determined as absolute values, but normalized as percentage compared to a group of standard controls included in the kit, assigning to the positive controls the value 100% and to the negative controls a value of 0%. The results of the above described experiment are shown in the following table:

| Protein | % relative to standards |
| --- | --- |
| ENA-78 | 17.4% |
| GCSF | 3.8% |
| GRO | 74.4% |
| GRO-alpha | 13% |
| IL-6 | 119.4% |
| IL-7 | 19.4% |
| IL-8 | 97.5% |
| MCP-1 | 53.2% |
| MCP-2 | 1.0% |
| MCSF | 4.4% |
| MDC | 5.0% |
| ANGIOGENIN | 11.5% |
| ONCOSTATIN m | 7.6% |
| VEGF | 13.3% |
| BDNF | 2.3% |
| BLC | 3.3% |
| CKb 8-1 | 6.0% |
| EOTAXIN 2 | 4.2% |

-continued

| Protein | % relative to standards |
|---|---|
| EOTAXIN 3 | 2.1% |
| FLT-3 LIGAND | 1.4% |
| FRACTALKINE | 6.1% |
| GCP-2 | 6.2% |
| GDNF | 5.1% |
| HGF | 8.6% |
| IGFBP-1 | 4.0% |
| IGFBP-2 | 10.3% |
| IGFBP-4 | 3.1% |
| IP-10 | 1.7% |
| LIF | 1.0% |
| LIGHT | 2.0% |
| MCP-4 | 20.8% |
| MIF | 4.6% |
| MIP-3alfa | 3.3% |
| NAP-2 | 8.6% |
| NT-3 | 11.4% |
| OSTEOPONTIN | 25.3% |
| OSTOPROTEGERIN | 12.0% |
| TGF-beta 2 | 1.68% |
| TIMP-1 | 23.4% |
| TIMP-2 | 48.4% |

Furthermore, cytokine array analysis did not detect in the conditioned medium of the invention the following proteins, as absent or present in concentrations below the array system detection limit: GM-CSF, I-309, IL-1 alpha, IL-1b, IL-2, IL-3, IL-4, IL-5, IL-10, IL-12 p40p70, IL-13, IL-15, IFN-gamma, MCP-3, MIG, MIP-1, RANTES, SCF, SDF-1, TARC, TGF-beta 1, TNF-alpha, TNF-beta, EGF, IGF-I, THROMBOPOIETIN, PDGF-bb, LEPTIN, EOTAXIN, FGF 4, FGF 6, FGF 7, FGF 9, IGFBP-3, IGFBP-4, IL-16, NT-4, PARC, PIGF, TGF-beta 3.

EXAMPLE 5

Evaluation of the Therapeutic Efficacy of the Conditioned Medium Obtained from PDMSC Cultures In order to evaluate the therapeutic efficacy of the conditioned medium of the invention, we conducted a series of studies using an in vitro model represented by placental villous explants derived from pregnancies affected by preeclampsia and fetal growth restriction. In particular, it was verified if the conditioned medium of the invention was able to reduce TNF-alpha expression levels in the above mentioned placental villous explants. TNF-alpha reduction was taken as sign of a significant anti-inflammatory activity. As previously described, several clinical and experimental evidences demonstrated that this potent pro-inflammatory cytokine is over-expressed in both the placenta and the serum of pregnant women affected by preeclampsia.

Cultures of 24 preeclamptic placental villous explants were treated for 48 hours with the conditioned medium obtained by culturing for 48 hours PDMSCs isolated from physiological pregnancies, as previously described in Example 3.

Placentas collection and tissue sampling were performed after delivery and after obtaining informed consent in accordance with the guidelines of the O.I.R.M. Sant' Anna and Mauriziano Hospitals ethical committee (Turin, Italy). The diagnosis of preeclampsia was made according to the following criteria: presence of pregnancy-induced hypertension (systolic ≥140 mmHg or diastolic ≥90 mmHg) and proteinuria (≥300 mg/24 h) after the 20th weeks of gestation in previously normotensive women. In total, twenty-four explants, formed by a villous tree portion characterized by preserved morphology and structure and of equal weight, were excised from the placental basal plate and cultured for 12 hours in 500 µl of HAM F12 medium without FBS at 37° C. and 5% $CO_2$ in order to equilibrate their conditions after the delivery-induced stress. After 12 hours, the culture medium was replaced with 500 µl of conditioned medium (in 12 explants) or with 500 µl of DMEM LG medium without serum (in 12 control explants). Explant cultures were incubated under the same experimental conditions for further 48 hours. Next, treated (12) and control (12) explants were collected and processed for mRNA isolation using TRIzol reagent (Invitrogen Life Technologies) following manufacturer instructions. After isolation, messenger RNA was purified by DNAse treatment (Sigma-Aldrich) in order to remove possible genomic DNA contaminations. RNA quality was assessed by spectrophotometric analysis at 260 nm wavelength, while its purity was determined by A260/A280 absorbance ratio at 1.8-2.

The cDNA (complementary DNA), which is necessary for the analysis of the TNF-alpha expression levels, was synthesized by RT-PCR starting from 5 µg of total RNA previously isolated. RT-PCR was performed using a random hexamers approach with the RevertAid H Minus First Strand cDNA Synthesis kit (Fermentas Life Science), following manufacturer instructions.

Variations of TNF-alpha gene expression levels following treatment of villous explants by the conditioned medium of the invention, were assessed by Real Time PCR using TaqMan primers and probes (Applied Biosystem). In order to perform a relative quantification, Real Time PCR data were compared between treated and control groups after being normalized for 18S ribosomal subunit data, used as internal reference.

Gene expression results, represented by the histogram in FIG. 1, clearly demonstrate that the treatment performed using the conditioned medium (CM) of the invention leaded to a statistically significant reduction of TNF-alpha levels in treated preeclamptic villous explants relative to controls (C) ($p=0.015$).

The invention claimed is:

1. A method of therapeutically treating pre-eclampsia comprising:
    obtaining a conditioned medium by culturing in vitro an isolated placental mesenchymal stem cell population from the placenta of a pregnant woman not affected by pre-eclampsia in a basal serum-free liquid culture medium for at least three hours,
    wherein the stem cell population has a chorionic or an amniotic origin,
    wherein the conditioned medium comprises at least the cell-secreted factors interleukin-6 (IL-6), interleukin-8 (IL-8) and monocyte chemoattractant protein 1 (MCP-1), and
    administering the conditioned medium to a subject in need thereof.

2. The method according to claim 1, wherein the conditioned medium is in a pharmaceutical form suitable for systemic administration.

3. The method according to claim 2, wherein the pharmaceutical form is suitable for administration by injection.

4. The method according to claim 1, wherein the conditioned medium comprises a further cell-secreted factor selected from the group consisting of ENA-78, GCSF, GRO, GRO-alpha, IL-7, MCP-2, MCSF, MDC, ANGIOGENIN, ONCOSTATIN m, VEGF, BDNF, BLC, CKb 8-1, EOTAXIN 2, EOTAXIN 3, FLT-3 LIGAND, FRAC- TALKINE, GCP-2, GDNF, HGF, IGFBP-1, IGFBP-2, IGFBP-4, IP-10, LIF, LIGHT, MCP-4, MIF, MIP-3alpha, NAP-2, NT-3, OSTEOPONTIN, OSTOPROTEGERIN, TGF-beta 2, TIMP-1, TIMP-2, RANTES, IGFBP-3, IL1 b, IL-3, MIP-1b, PlGF, IL-1a, I309, FGF9, TARC, PDGF-bb, LEPTIN, TNF-alpha and any combination thereof.

* * * * *